United States Patent
Lavigne et al.

(10) Patent No.: US 9,592,108 B2
(45) Date of Patent: Mar. 14, 2017

(54) SYSTEM AND METHOD OF LAPAROSCOPIC USE OF HEMOSTATIC PATCH

(75) Inventors: Kevin Lavigne, Hamden, CT (US);
Steven Bennett, Cheshire, CT (US);
Nathaniel Mast, Hamden, CT (US)

(73) Assignee: Covidien LP, Mansfield, MA (US)

( * ) Notice: Subject to any disclaimer, the term of this patent is extended or adjusted under 35 U.S.C. 154(b) by 1847 days.

(21) Appl. No.: 12/791,534

(22) Filed: Jun. 1, 2010

(65) Prior Publication Data

US 2011/0029003 A1 Feb. 3, 2011

Related U.S. Application Data

(60) Provisional application No. 61/229,333, filed on Jul. 29, 2009.

(51) Int. Cl.
| | | |
|---|---|---|
| A61B 17/03 | (2006.01) | |
| A61F 2/00 | (2006.01) | |
| A61L 27/34 | (2006.01) | |
| A61L 27/52 | (2006.01) | |
| A61B 17/34 | (2006.01) | |

(52) U.S. Cl.
CPC ............ A61F 2/0063 (2013.01); A61L 27/34 (2013.01); A61L 27/52 (2013.01); *A61B 17/3468* (2013.01)

(58) Field of Classification Search
USPC ......... 606/151; 128/898; 604/500, 506, 511; 424/423
See application file for complete search history.

(56) References Cited

U.S. PATENT DOCUMENTS

| | | |
|---|---|---|
| 3,364,200 A | 1/1968 | Ashton et al. |
| 4,626,253 A | 12/1986 | Broadnax, Jr. |
| 5,201,745 A | 4/1993 | Tayot et al. |
| 5,397,332 A | 3/1995 | Kammerer et al. |
| 5,484,913 A | 1/1996 | Stilwell et al. |
| 6,152,943 A | 11/2000 | Sawhney |
| 6,165,201 A | 12/2000 | Sawhney et al. |
| 6,179,862 B1 | 1/2001 | Sawhney |
| 6,443,964 B1 | 9/2002 | Ory et al. |
| 6,500,777 B1 | 12/2002 | Wiseman et al. |
| 6,514,534 B1 | 2/2003 | Sawhney |
| 6,566,406 B1 | 5/2003 | Pathak et al. |

(Continued)

FOREIGN PATENT DOCUMENTS

| | | |
|---|---|---|
| EP | 1707130 A1 | 10/2006 |
| EP | 2177239 A2 | 4/2010 |

(Continued)

OTHER PUBLICATIONS

European Search Report for EP 09252417.2-1219 mailed Dec. 12, 2010.

(Continued)

*Primary Examiner* — Julie A Szpira (57) ABSTRACT

The present disclosure includes systems and a method for in situ application of a surgical patch during minimally invasive surgery. The method includes the steps of inserting a surgical patch into a bag; transferring a polymeric bag containing a hemostatic patch into a body cavity; removing the surgical patch from the polymeric bag while the polymeric bag is within the body cavity; and applying the surgical patch to a tissue within the body cavity.

5 Claims, 5 Drawing Sheets

(56) References Cited

U.S. PATENT DOCUMENTS

| | | | |
|---|---|---|---|
| 6,605,294 B2 | 8/2003 | Sawhney | |
| 6,673,093 B1 | 1/2004 | Sawhney | |
| 6,703,047 B2 | 3/2004 | Sawhney et al. | |
| 6,818,018 B1 | 11/2004 | Sawhney | |
| 6,946,003 B1* | 9/2005 | Wolowacz et al. | 623/23.72 |
| 7,009,034 B2 | 3/2006 | Pathak et al. | |
| 7,021,086 B2 | 4/2006 | Ory et al. | |
| 7,347,850 B2 | 3/2008 | Sawhney | |
| 2002/0106409 A1 | 8/2002 | Sawhney et al. | |
| 2003/0031697 A1 | 2/2003 | Chudzik et al. | |
| 2004/0092970 A1* | 5/2004 | Xavier | 606/151 |
| 2006/0200169 A1 | 9/2006 | Sniffin | |
| 2006/0200170 A1 | 9/2006 | Aranyi | |
| 2006/0229640 A1 | 10/2006 | Whitfield | |
| 2008/0082113 A1* | 4/2008 | Bishop et al. | 606/151 |
| 2010/0042045 A1* | 2/2010 | Splvey | 604/93.01 |
| 2011/0070288 A1 | 3/2011 | Andjelic | |

FOREIGN PATENT DOCUMENTS

| | | |
|---|---|---|
| EP | 2179753 A2 | 4/2010 |
| GB | 2459902 A | 11/2009 |
| WO | WO2004/037123 A1 | 5/2004 |
| WO | WO2007/081940 A2 | 7/2007 |
| WO | WO2010/019655 | 2/2010 |
| WO | WO 2010/043980 A2 | 4/2010 |

OTHER PUBLICATIONS

European Search Report for EP 09252421.4-1219 mailed Dec. 12, 2010.
Canadian Office Action issued in corresponding Canadian Application No. 2,709,046 dated Mar. 29, 2016.

* cited by examiner

SYSTEM AND METHOD OF LAPAROSCOPIC USE OF HEMOSTATIC PATCH

CROSS-REFERENCE TO RELATED APPLICATIONS

This application claims the benefit of and priority to U.S. Provisional Patent Application No. 61/229,333, filed Jul. 29, 2009, the entire disclosure of which is incorporated by reference herein.

BACKGROUND

Technical Field

The present disclosure relates to apparatus and methods for the application of a surgical patch. More particularly, the present disclosure relates to systems and methods for the in situ application of a surgical patch during minimally invasive surgery.

Background

Surgical patches, such as hemostatic patches, are used in repair of defective tissues or organs to establish hemostasis. Hemostatic patches can be used as a supplement to or in conjunction with sutures, staples, or other medical attachment or fastening devices. Hemostatic patches can be used to provide hemostasis to the tissue or organ in need of treatment.

Self-affixing surgical patches are useful for application during open surgery where the surgical patch is applied in the form, i.e., shape, in which it is packaged. However, certain types of absorbable medical devices may be moisture sensitive, that is, they will prematurely react if exposed to moisture in the atmosphere or in the body. Therefore, an apparatus and method of transporting these patches without exposure to ambient or interstitial moisture is needed.

SUMMARY

The present disclosure is directed to the application of a surgical patch during minimally invasive surgery. The method includes laparoscopically transferring a polymeric bag containing a surgical patch into a body cavity followed by removing said surgical patch from the polymeric bag within the body cavity, and applying said surgical patch to a site in the body cavity in need of hemostasis. The method may also include the step of providing a hemostatic patch. The hemostatic patch may include a substrate having a first hydrogel precursor applied to a first portion of the substrate; and a second hydrogel precursor applied to a second portion of the substrate. The method may also include the step of providing a polymeric bag comprising a material selected from polyurethane and latex.

In another embodiment the surgical patch is transferred to a polymeric bag. The polymeric bag containing the surgical patch is then laparoscopicly transferred into a body cavity. This embodiment may further include providing a hemostatic patch. The hemostatic patch may include a substrate having a first hydrogel precursor applied to a first portion of the substrate; and a second hydrogel precursor applied to a second portion of the substrate. The polymeric bag may include a material selected from polyurethane and latex.

The present disclosure further includes an apparatus for transferring an item into a body cavity during laparoscopic surgery. The apparatus may include a surgical patch in a polymeric bag sized and dimensioned to be received within a deployment device.

The present disclosure is also directed to an apparatus for performing a surgical procedure. The apparatus includes: an elongated tube; a drive rod; a spring; and a surgical patch received with a polymeric bag. The drive rod, spring, and surgical patch are slidably housed within the elongated tube. The distal end of the drive rod may be connected to the spring. The proximal end of the drive rod may include a handle.

BRIEF DESCRIPTION OF THE DRAWINGS

The foregoing objects and advantages of the disclosure will become more apparent from the reading of the following description in connection with the accompanying drawings, in which.

DETAILED DESCRIPTION

The present disclosure relates to devices, systems and methods for minimally invasive surgeries such as, endoscopic, laparoscopic, arthroscopic, endoluminal and/or transluminal placement of a surgical patch at a surgical site. As used herein the term "surgical patch" is used to refer to any type of patch for use in surgical procedures, such as, for example, patches that react in situ and those that react upon exposure to moisture. As used herein the term "laparoscopic deployment device" is used to refer to a deployment device that may be used during minimally invasive surgeries described above.

In the drawings and in the description that follows, the term "proximal," as is traditional, will refer to an end of a device that is closer to the user, while the term "distal" will refer to the end of the device that is further from the user.

Laparoscopic surgical procedures are minimally invasive procedures which are carried out within the body cavity through use of access ports in conjuncture with elongated surgical devices. An initial opening in the body tissue enables passage of the endoscopic or laparoscopic device to the interior of the body. Openings include natural passageways of the body or openings which are created by a tissue piercing device such as a trocar. During laparoscopic procedures, narrow punctures or incisions are made minimizing trauma to the body cavity and reducing patient recovery time.

Figure 1:
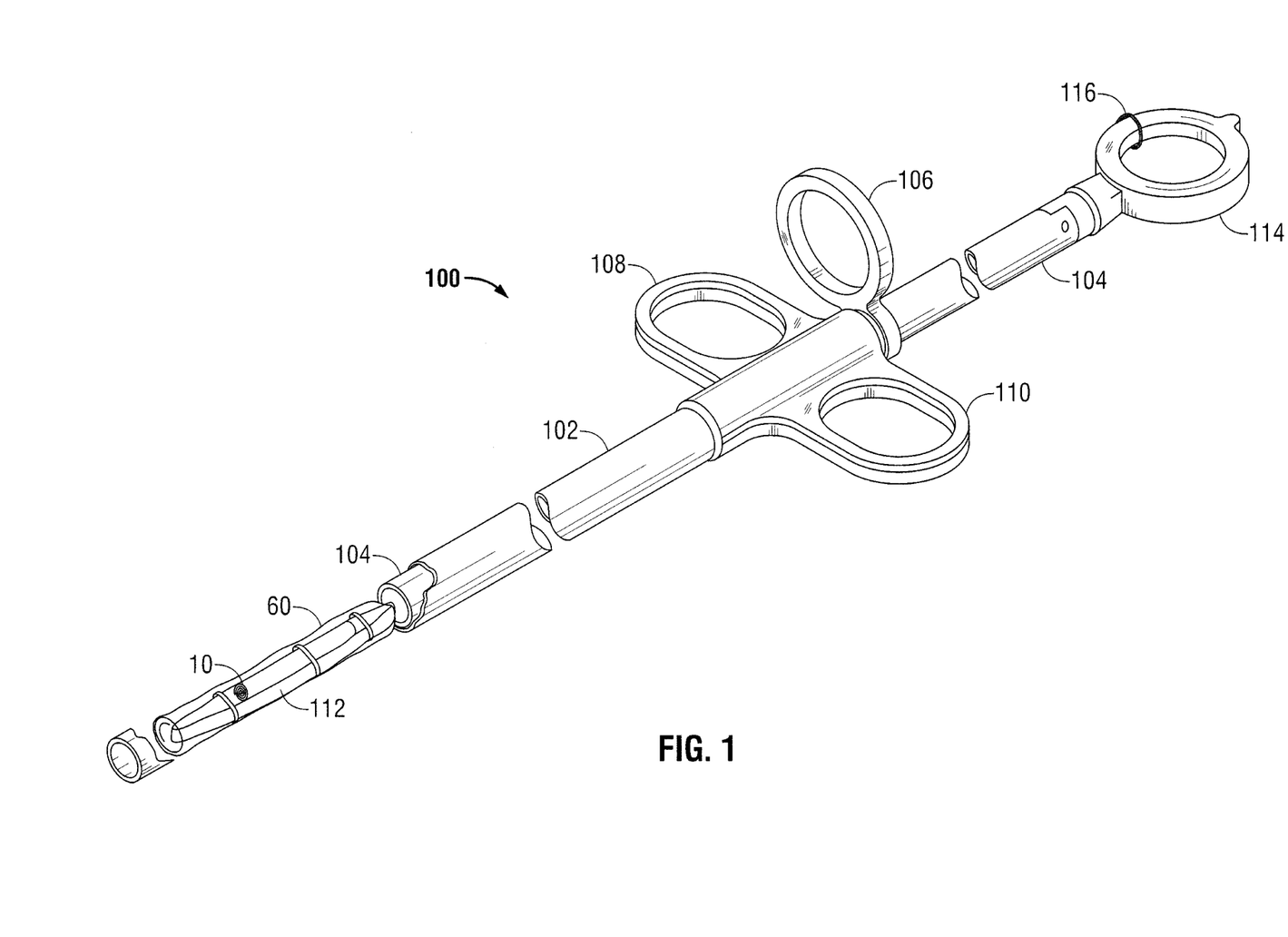
FIG. 1 is a perspective view of a laparoscopic deployment device, shown in a non-deployed condition, in accordance with the present disclosure.

Referring now in specific detail to the drawings, in which like numbers identify similar or identical elements, FIG. 1 illustrates a laparoscopic deployment/collection device and is generally designated as 100. The deployment device 100 includes an elongated tube 102, which is of such dimensions and/or diameter to be insertable through an access device, such as a trocar cannula, for endoscopic or laparoscopic procedures. The tube 102 is generally between about 0.25 inches to 0.50 inches in diameter, and about 10 inches to about 15 inches long, although other dimensions may also be used if appropriate. Tube 102 slidably houses a drive rod 104 and, when undeployed, a polymeric bag 60, containing a surgical patch 10.

The laparoscopic deployment device 100 includes a drive rod or bar 104 that is an elongated generally cylindrical member slidably disposed through the bore of tube 102. A distal end of the drive rod 104 is attached to the bag 60 to move the bag 60 from a non-deployed position contained within the outer tube 102 to a deployed position distal to the outer tube 102.

A locking tab 106 may be included to prevent premature actuation of the device. The locking tab 106 includes snap fit engagement structure to engage a slot of the drive rod 104. When thus engaged, the drive rod 104 cannot be pushed distally beyond the point where the locking tab 106 engages the proximal end of handle portions 108, 110.

In addition, the laparoscopic deployment device 100 may include a finger loop 114 for engagement by a user's finger. One end of a drawstring 116 is attached to the finger loop 114 while an opposing end of the drawstring 116 is attached to the bag 60. In an initial, unused condition, bag 60 will be rolled up (or otherwise folded) and contain a spring 112 and surgical patch 10 in a relatively straight position within tube 102. When the drive rod 104 is advanced, the spring 112 connected thereto will exit a distal end of tube 102 and resiliently open, thereby deploying and opening the bag 60 to allow access to the surgical patch 10. In some embodiments the bag 60 will remain closed following deployment. Tube 102 is preferably formed from a metal such as stainless steel and is preferably coated with a shrink-wrap plastic such as shrinkable polyethylene fiberglass, or polyvinyl chloride of a grade suitable for use in surgical procedures.

Such devices are known in the art and include, for example, the devices disclosed in U.S. Patent Application Publication No. 2006/0229640, filed Mar. 29, 2005; U.S. Patent Application Publication No. U.S. 2006/0200170, filed Mar. 7, 2005; and U.S. Patent Application Publication No. 2006/0200169, filed Mar. 7, 2005, the entire contents of which are incorporated by reference herein.

Figure 2:
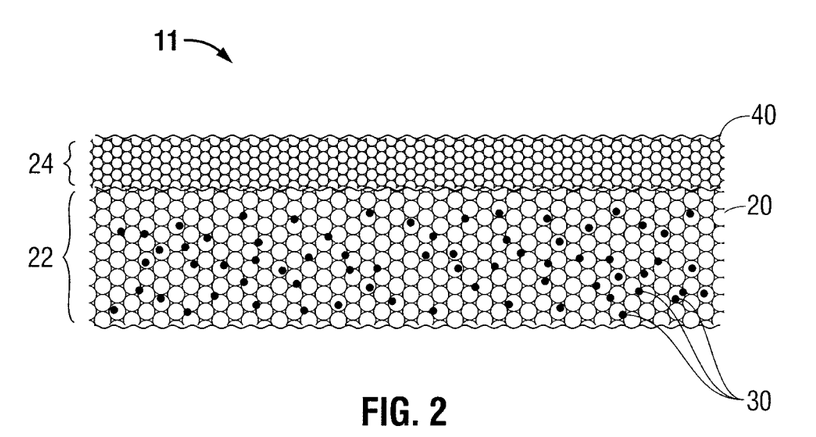
FIG. 2 is an illustration of a hemostatic patch in accordance with the present disclosure.

FIG. 2 illustrates one embodiment of a surgical patch, according to the present disclosure. A hemostatic patch 11 is used with laparoscopic deployment device 100. The hemostatic patch 11 includes a porous substrate 20 having a first hydrogel precursor 30 applied to a first portion 22 of the porous substrate and a second hydrogel precursor 40 applied to a second portion 24 of the porous substrate. Such a hemostatic patch 11 is disclosed in U.S. Provisional Patent Application No. 61/196,543, filed Oct. 17, 2008, the entire contents of which are incorporated by reference herein.

During use, the hemostatic patch 11 is oriented with the portion 24 to which the second hydrogel precursor 40 is applied being closer to the tissue and the portion 22 having the first hydrogel precursor 30 applied thereto further from the tissue. In embodiments, the first and second portions 22, 24 may be distinguishable from one another by the addition of contrast dyes, surface texturing, coloring or other visual cues. Upon contact with tissue, such as, for example, injured tissue, the hemostatic patch 11 will soak up physiological fluid and the second hydrogel precursor 40 may be dissolved by the fluid. As the fluid wicks into and migrates across the hemostatic patch 11, it will carry the dissolved second hydrogel precursor 40 along through the hemostatic patch 11. Eventually, the fluid will migrate through the hemostatic patch 11 sufficiently to reach the portion 22 to which the first hydrogel precursor 30 is applied, thereby contacting the first hydrogel precursor 30. The first and second hydrogel precursors 30, 40 will then react to form a biocompatible cross-linked material, thereby creating hemostasis at the injury site. In some embodiments, the biocompatible cross-linked material produced by reaction of the first and second hydrogel precursors 30, 40 not only provide hemostatic properties but also provide a portion of the hemostatic patch 11 with anti-adhesive properties.

The porous substrate 20 of the hemostatic patch 11 has openings or pores over at least a portion of a surface thereof. The pores may be formed in the substrate either before or after implantation. As described in more detail below, suitable materials for forming the porous substrate 20 include, but are not limited to fibrous structures (e.g., knitted structures, woven structures, non-woven structures, etc.) and/or foams (e.g., open or closed cell foams). In embodiments, the pores may be in sufficient number and size so as to interconnect across the entire thickness of the porous substrate 20. Woven fabrics, kitted fabrics and open cell foam are illustrative examples of structures in which the pores can be in sufficient number and size so as to interconnect across the entire thickness of the porous substrate 20. In embodiments, the pores do not interconnect across the entire thickness of the porous substrate 20. Closed cell foam or fused non-woven materials are illustrative examples of structures in which the pores may not interconnect across the entire thickness of the porous substrate 20. The pores of the foam porous substrate 20 may span across the entire thickness of porous substrate 20. In yet other embodiments, the pores do not extend across the entire thickness of the porous substrate 20, but rather are present at a portion of the thickness thereof. In embodiments, the openings or pores are located on a portion of the surface of the porous substrate 20, with other portions of the porous substrate 20 having a non-porous texture. In other embodiments, the pores may be formed after implantation in situ. The in situ pore formation may be performed using any suitable method. Some non-limiting examples include the use of contact lithography, living radical photopolymer (LRPP) systems and salt leaching. Those skilled in the art reading the present disclosure will envision other pore distribution patterns and configurations for the porous substrate 20.

Where the porous substrate 20 is fibrous, the fibers may be filaments or threads suitable for knitting or weaving or may be staple fibers, such as those frequently used for preparing non-woven materials. The fibers may be made from any biocompatible material. Thus, the fibers may be formed from a natural material or a synthetic material. The material from which the fibers are formed may be bioabsorbable or non-bioabsorbable. It should be understood that any combination of natural, synthetic, bioabsorbable and non-bioabsorbable materials may be used to form the fibers. Some non-limiting examples of materials from which the fibers may be made include, but are not limited to polyesters such as poly(lactic acid) and poly(glycolic acid) poly(trimethylene carbonate), poly (dioxanone), poly (hydroxybutyrate), poly (phosphazine), polyethylene terephthalate, ultra-high molecular weight polyethylene, polyethylene glycols, polyethylene oxides, polyacrylamides, polyhydroxyethylmethylacrylate (pHEMA), polyvinylpyrrolidone, polyvinyl alcohols, polyacrylic acid, polyacetate, polycaprolactone, polypropylene, aliphatic polyesters, glycerols, poly(amino acids), copoly (ether-esters), polyalkylene oxalates, poly (saccharides), polyamides, poly (iminocarbonates), polyalkylene oxalates, polyoxaesters, polyorthoesters, polyphosphazenes, biopolymers, polymer drugs and copolymers, block copolymers, homopolymers, blends and combinations thereof.

Where the porous substrate 20 is fibrous, the porous substrate 20 may be formed using any method suitable to forming fibrous structures, including but not limited to knitting, weaving, non-woven techniques, wet-spinning, electro-spinning, extrusion, co-extrusion, and the like. Suitable techniques for making fibrous structures are within the purview of those skilled in the art. In embodiments, the textile has a three dimensional structure, such as the textiles described in U.S. Pat. Nos. 7,021,086 and 6,443,964, the contents of which are incorporated by reference herein.

In some embodiments, the porous substrate 20 is made from fibers of oxidized cellulose. Such materials are known and include oxidized cellulose hemostat materials commercially available under the trade name SURGICEL®. Methods for preparing oxidized cellulose hemostat materials are known to those skilled in the art and are disclosed, for example in U.S. Pat. Nos. 3,364,200; 4,626,253; 5,484,913; and 6,500,777, the disclosures of which are incorporated herein by this reference in their entirety.

Where the porous substrate 20 is a foam, the porous substrate 20 may be formed using any method suitable to forming a foam or sponge including, but not limited to the lyophilization or freeze-drying of a composition. The foam may be cross-linked or non-cross-linked, and may include covalent or ionic bonds. Suitable techniques for making foams are within the purview of those skilled in the art.

As mentioned above, the porous substrate 20 has a first and second hydrogel precursor 30, 40 applied thereto. The terms "first hydrogel precursor" and "second hydrogel precursor" each mean a polymer, functional polymer, macromolecule, small molecule, or crosslinker that can take part in a reaction to form a network of crosslinked molecules, e.g., a hydrogel.

In embodiments, each of the first and second hydrogel precursors 20, 30, includes only one category of functional groups, either only nucleophilic groups or only electrophilic functional groups, so long as both nucleophilic and electrophilic precursors are used in the crosslinking reaction. Thus, for example, if the first hydrogel precursor 30 has nucleophilic functional groups such as amines, the second hydrogel precursor 40 may have electrophilic functional groups such as N-hydroxysuccinimides. On the other hand, if first hydrogel presursor 30 has electrophilic functional groups such as sulfosuccinimides, then the second hydrogel precursor 40 may have nucleophilic functional groups such as amines or thiols. Thus, functional polymers such as proteins, poly(allyl amine), styrene sulfonic acid, or amine-terminated di- or multifunctional poly(ethylene glycol) ("PEG") can be used.

The first and second hydrogel precursors 30, 40 may have biologically inert and water soluble cores. When the core is a polymeric region that is water soluble, preferred polymers that may be used include: polyether, for example, polyalkylene oxides such as polyethylene glycol("PEG"), polyethylene oxide ("PEO"), polyethylene oxide-co-polypropylene oxide ("PPO"), co-polyethylene oxide block or random copolymers, and polyvinyl alcohol ("PVA"); poly(vinyl pyrrolidinone) ("PVP"); poly(amino acids); poly (saccharides), such as dextran, chitosan, alginates, carboxymethylcellulose, oxidized cellulose, hydroxyethylcellulose, hydroxynethylcellulose, hyaluronic acid, and proteins such as albumin, collagen, casein, and gelatin. The polyethers and more particularly poly(oxyalkylenes) or poly(ethylene glycol) or polyethylene glycol are especially useful. When the core is small molecular in nature, any of a variety of hydrophilic functionalities can be used to make the first and second hydrogel precursors 30, 40 water soluble. For example, functional groups like hydroxyl, amine, sulfonate and carboxylate, which are water soluble, maybe used to make the precursor water soluble. In addition, N-hydroxysuccinimide ("NHS") ester of subaric acid is insoluble in water, but by adding a sulfonate group to the succinimide ring, the NHS ester of subaric acid may be made water soluble, without affecting its reactivity towards amine groups.

The first and second hydrogel precursors 30, 40 may be applied to the porous substrate 20 using any suitable method known to those skilled in the art. For example, the first and second hydrogel precursors 30, 40, may be incorporated into the porous substrate 20 prior to forming the porous substrate 20. In another non-limiting example, the first or second hydrogel precursors 30, 40 may be positioned in the pores of the porous substrate 20 or onto a surface of the porous substrate 20 following formation of the substrate. In additional embodiments, the porous substrate 20 may be calendered prior to application of the first hydrogel precursor 30 thereby allowing the first or second hydrogel precursors 30, 40 to penetrate into openings on the substrate which were created by the calendaring process.

In other embodiments, the first or second hydrogel precursors 30, 40 may be in the form of a coating which is applied to the substrate in any concentration, dimension and configuration capable of forming the hemostatic patch 11. The coating may form a non-porous layer or a porous layer. In embodiments, at least one of the first and second hydrogel precursors 30, 40 is a cross-linker. In embodiments, at least one of the first and second hydrogel precursors 30, 40 is a macromolecule, and is referred to as a "functional polymer".

Each of the first and second hydrogel precursors 30, 40 is multifunctional, meaning that it comprises two or more electrophilic or nucleophilic functional groups, such that, for example, a nucleophilic functional group on the first hydrogel precursor 30 may react with an electrophilic functional group on the second hydrogel precursor 40 to form a covalent bond. At least one of the first or second hydrogel precursors 30, 40 includes more than two functional groups, so that, as a result of electrophilic-nucleophilic reactions, the precursors combine to form cross-linked polymeric products.

In embodiments, a multifunctional nucleophilic polymer such as trilysine may be used as a first hydrogel precursor 30 and a multifunctional electrophilic polymer such as a multi-arm PEG functionalized with multiple NHS groups may be used as a second hydrogel precursor 40. The multi-arm PEG functionalized with multiple NHS groups can for example have four, six or eight arms and have a molecular weight of from about 5,000 to about 25,000. Many other examples of suitable first and second hydrogel precursors 30, 40 are described in U.S. Pat. Nos. 6,152,943; 6,165,201; 6,179,862; 6,514,534; 6,566,406; 6,605,294; 6,673,093; 6,703,047; 6,818,018; 7,009,034; and 7,347,850, the entire content of each of which is incorporated herein by reference.

While the present disclosure may involve a hemostatic patch, any surgical patch may be used in the method disclosed herein. The hemostatic patch may be any size and dimension capable of transport in the laparoscopic deployment device of the disclosure. In one embodiment, the hemostatic patch is about 2 inches square, although it is envisioned that the patch may be of varying shapes and sizes. Additionally, while the substrate used in forming the patch is described as "porous" the substrate may be porous or non-porous in various embodiments.

Upon application to a site of bleeding tissue, the hemostatic patch may affect hemostasis of said tissue. As used herein, the term "hemostasis" means the arrest of bleeding. It is believed, without being limited thereto, that the hemostatic effect of the hemostatic patch is due to both intrinsic and extrinsic factors. In some embodiments, the substrate may be comprised of a hemostatic agent providing an intrinsic hemostatic effect. In embodiments, the cross-linking between the hydrogel precursors creates a physical barrier to blood flow providing an extrinsic hemostatic effect. Hemostasis may occur, at the site of application of the hemostatic patch, within less than about 2 minutes. As stated above, upon contact with tissue, such as, for example, injured or bleeding tissue, the hemostatic patch 11 soaks up interstitial and physiological fluid (e.g., blood, lymph-fluid, etc.) and the first and second hydrogel precursors 30, 40 are mixed by the fluid. In order to prevent the hemostatic patch 11 from taking up fluid prior to use at the location in need of hemostasis, the hemostatic patch 11 is retained or sealed in packaging until the time it is needed for its application.

Figure 3:
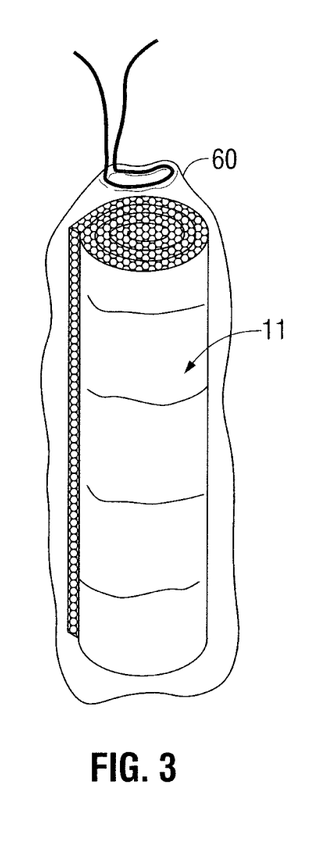
FIG. 3 is an illustration of a hemostatic patch retained within a polymeric bag in accordance with the present disclosure.

As shown in FIG. 3, to provide for moisture resistant transport of the hemostatic patch 11 during laparoscopic surgery, the hemostatic patch 11 is enclosed in a polymeric bag 60, which is moisture resistant. The term "moisture" as used herein means physiological fluids and humidity. As used herein, the term "sterile" means that the bag is free from living organisms such as microorganisms in addition to endotoxins, viruses, and the like. The bag 60 may be formed of material that resists moisture/humidity. Exemplary materials which may be used in accordance with the present disclosure include, for example, a substantially transparent polymeric material such as a polyurethane sheet or latex. In embodiments, the bag 60 may include a metalized layer disposed on a plastic film backing in order to reduce the incidence and degree of porosity thereof. In one embodiment, the bag 60 is formed from aromatic polyester type thermoplastic polyurethane such as Dureflex®, a product of Deerfield Urethane, Inc., located in Whately, Mass. In some embodiments, the bag 60 is transparent to permit viewing of the hemostatic patch 10. The thickness of the bag 60 can be from about 0.001 to about 0.005 inches although other thicknesses are also envisioned. The bag 60 should also be impervious to penetration by disease-causing cells, such as cancer cells. The bag 60 may be of any dimension suitable to enclose the hemostatic patch 11, and prevent the hemostatic patch from contacting moisture. The bag 60 may be folded or rolled to a size sufficient to be inserted into the laparoscopic deployment device 100. In some embodiments, the bag 60 may have a diameter from about 1.5 inches to about 6.0 inches, a depth of from about 2 inches to about 10 inches, and a cubic capacity of up to about 2.0 liters of water. In some embodiments, the bag 60 is an Endobag™ manufactured by Covidien AG, Mansfield, Mass. As seen in FIG. 3, hemostatic patch 11 may be rolled or folded for placement within bag 60. In some embodiments, when folded or rolled, the hemostatic patch 11, in the bag 60, is preferably less than about 0.50 inches in diameter. In another embodiment, the rolled or folded hemostatic patch 11, in the bag 60, is less than about 0.25 inches in diameter.

The polymeric bag 60 may be sealed in such a manner as to protect the hemostatic patch 11 from exposure to moisture during and after deployment thereof from a laparoscopic device 100. In embodiments, the bag 60 may be open following deployment from the device.

Figure 4A:
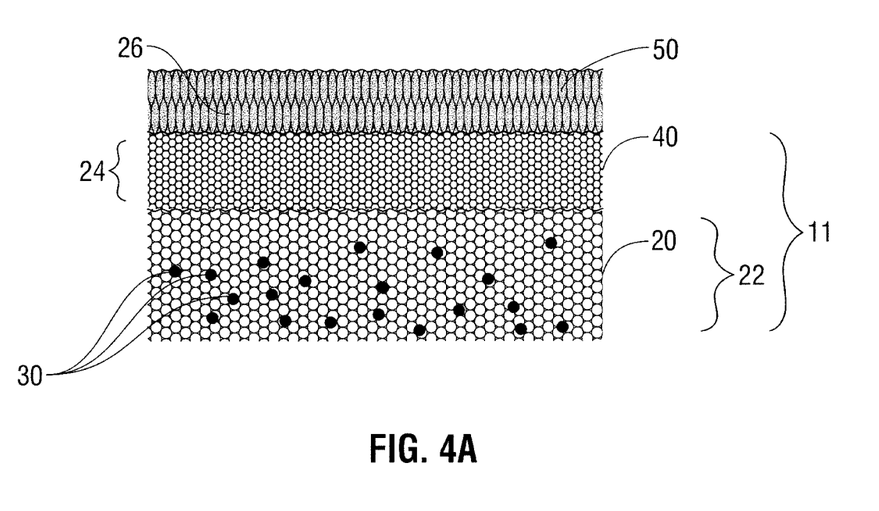
FIGS. 4A-4B are a schematic illustration of the effect of fluid on the hemostatic patch in situ in accordance with the present disclosure.
Figure 4B:
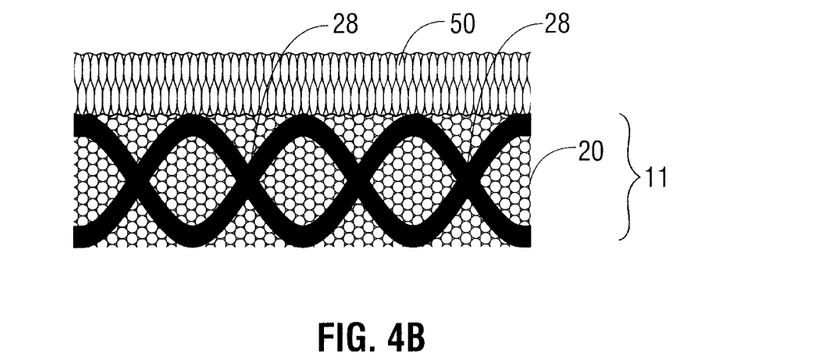

The hemostatic patch 11, in the sterile polymeric bag 60, may be transferred to a body cavity during laparoscopic surgery utilizing laparoscopic deployment device 100. As seen in FIGS. 4A-4B, during use, the hemostatic patch 11 is oriented with second portion 24, to which the second hydrogel precursor 40 is applied, being closer to tissue 50 and with the first portion 22, to which the first hydrogel precursor 30 is applied, being disposed further from the tissue 50. Upon contact with tissue 50, such as, for example, injured or bleeding tissue, hemostatic patch 11, soaks up physiological fluid or blood 26 and the second portion 24, having the second hydrogel precursor 40, is dissolved by the fluid or blood 26. As the fluid or blood 26 wicks into and migrates across the hemostatic patch 11, the fluid or blood carries the dissolved second hydrogel precursor 40 along through the hemostatic patch 11 sufficiently to reach the first portion 22 to which the first hydrogel precursor 30 is applied, thereby initiating the cross-linking reaction between the first and second hydrogel precursors 30, 40. At this point, as seen in FIG. 4B, first and second hydrogel precursors 30, 40, then react to form a biocompatible cross-linked material 28 thereby assisting with the hemostasis of the tissue 50.

In one embodiment, the laparoscopic deployment device 100 may contain the hemostatic patch 11 encased in the polymeric bag 60 for delivery during a single use of the laparoscopic deployment device. In another embodiment, a hemostatic patch 11, encased in the polymeric bag 60, may be provided for insertion into a laparoscopic deployment device 100.

Figure 5A:
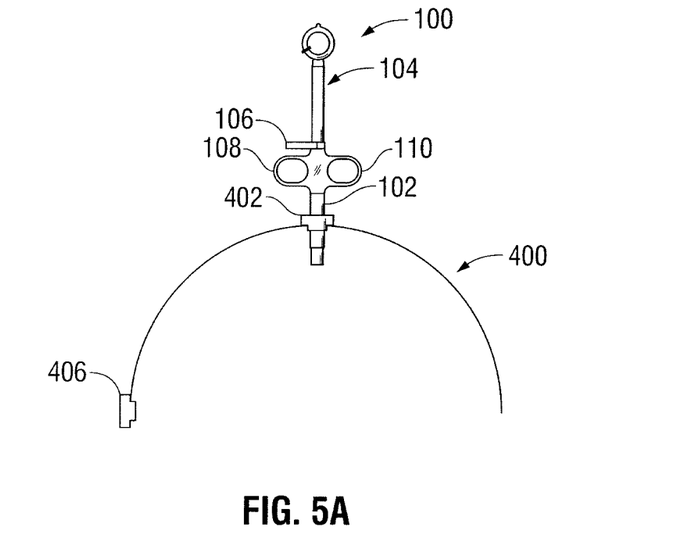
FIGS. 5A-5D are schematic illustrations of the use of the laparoscopic deployment device of FIG. 1 deploying the hemostatic patch retained within a bag of FIG. 2 in accordance with the present disclosure.
Figure 5B:
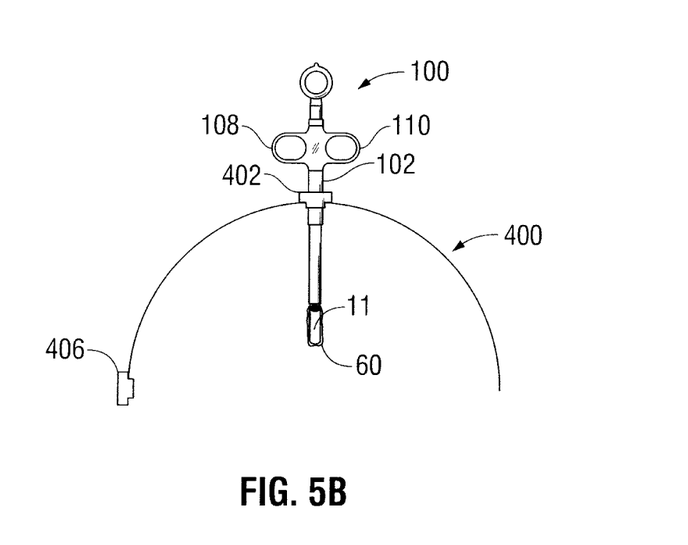
Figure 5C:
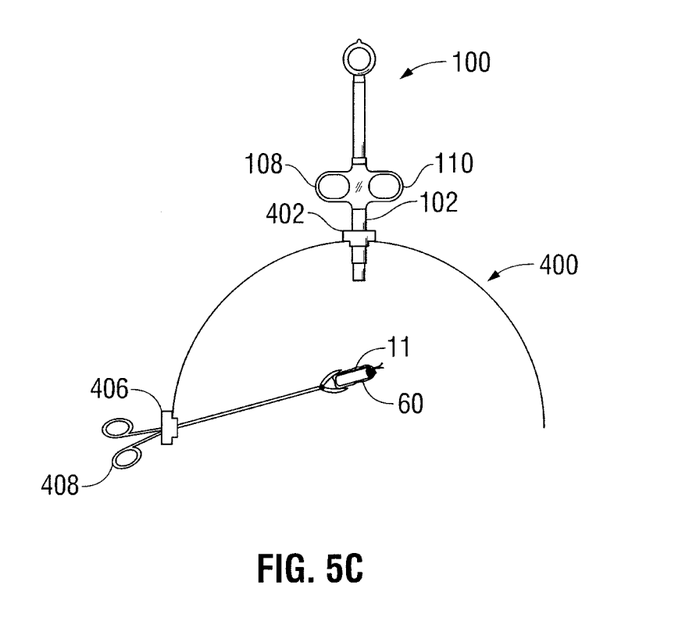
Figure 5D:
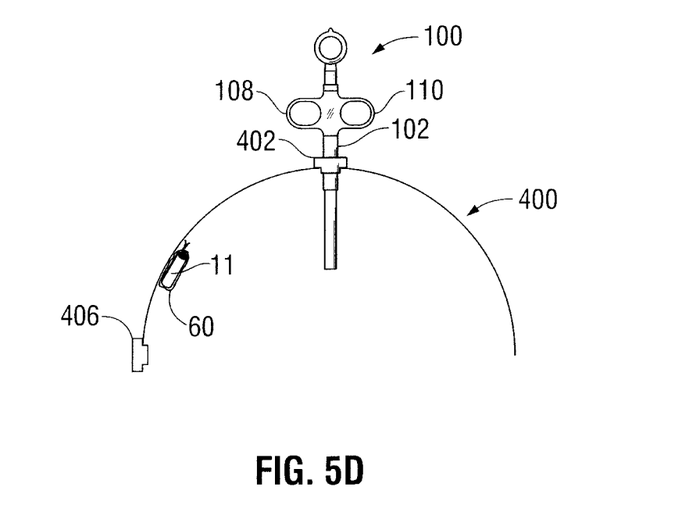

According to another method of use, as shown in FIGS. 5A-5C, a laparoscopic deployment device 100 is shown inserted into a body cavity 400 through a trocar 402 and additional trocar 406 is inserted in the side of the body cavity 400, for later use. As shown in FIGS. 5A-5B, locking tab 106 is removed and drive rod 104 is pushed to the proximal end of handle portions 108, 110. As seen in FIG. 5B, the hemostatic patch 11, encased in the polymeric bag 60 is deployed though the laparoscopic deployment device 100 into the body cavity 400. At this point, as seen in FIG. 5C, the encased hemostatic patch 11 can then be removed from laparoscopic deployment device 100 using pinchers 408 through trocar 406 and held to the side of the body cavity 400 as shown in FIG. 5D, until needed. At the point in time of the procedure/operation, when the hemostatic patch 11 is needed, various laparoscopic tools known to those skilled in the art can be utilized to remove the hemostatic patch 11 from the polymeric bag 60 and place the hemostatic patch 11 in the location it is needed or desired, e.g., the injured or bleeding tissue.

While the above description contains many specifics, these specifics should not be construed as limitations on the scope of the present disclosure, but merely as exemplifications of preferred embodiments thereof. Those skilled in the art will envision many other possible variations that are within the scope and spirit of the present disclosure.

What is claimed is:

1. A method for in situ application of a surgical patch during minimally invasive surgery, the method comprising the steps of:
    providing a surgical patch comprising:
        a substrate having a first hydrogel precursor applied to a first portion of the substrate; and
        a second hydrogel precursor applied to a second portion of the substrate;
    inserting the surgical patch into a polymeric bag;
    transferring the polymeric bag containing the surgical patch into a body cavity;
    removing the surgical patch from the polymeric bag while the polymeric bag is within the body cavity; and applying the surgical patch to a tissue within the body cavity by orienting the second portion of the substrate having the second hydrogel precursor closer to the tissue and the first portion of the substrate having the first hydrogel precursor further from the tissue.

2. A method according to claim 1, further comprising the step of providing a polymeric bag comprising a material selected from the group consisting of polyurethane and latex.

3. The method according to claim 1 further including the step of:
creating hemostasis along the tissue by dissolving the second hydrogel precursor with physiological fluid and allowing the fluid to migrate through the surgical path towards the first portion thereby contacting the first hydrogel precursor, wherein the first and second hydrogel precursors react to form a biocompatible cross-linked material.

4. A method for inserting a surgical patch into a body cavity, the method comprising the steps of:
providing a surgical patch comprising:
a substrate having a first hydrogel precursor applied to a first portion of the substrate; and
a second hydrogel precursor applied to a second portion of the substrate;
transferring a surgical patch into a polymeric bag; and
laparoscopically inserting the polymeric bag containing the surgical patch, into a body cavity by orienting the second portion of the substrate having the second hydrogel precursor closer to a tissue of the body cavity.

5. A method according to claim 4, further comprising providing a polymeric bag comprising a material selected from the group consisting of polyurethane and latex.

* * * * *